(12) United States Patent
Li et al.

(10) Patent No.: US 7,208,290 B2
(45) Date of Patent: Apr. 24, 2007

(54) METHODS OF CO-EXPRESSING UMAMI TASTE RECEPTORS AND CHIMERIC $G\alpha_{15}$ VARIANTS

(75) Inventors: Xiaodong Li, San Diego, CA (US); Hong Xu, San Diego, CA (US); Lena Staszewski, San Diego, CA (US); Jon Elliot Adler, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 534 days.

(21) Appl. No.: 10/318,031

(22) Filed: Dec. 13, 2002
(Under 37 CFR 1.47)

(65) Prior Publication Data
US 2003/0220479 A1    Nov. 27, 2003

Related U.S. Application Data

(60) Provisional application No. 60/399,466, filed on Jul. 29, 2002.

(51) Int. Cl.
*C12P 21/06* (2006.01)
*C12N 1/20* (2006.01)
*C12N 15/74* (2006.01)

(52) U.S. Cl. .................. 435/69.1; 435/252.3; 435/471; 530/402

(58) Field of Classification Search ...................... None
See application file for complete search history.

(56) References Cited

U.S. PATENT DOCUMENTS 6,004,808 A * 12/1999 Negulescu et al. .......... 435/325
2002/0160424 A1 * 10/2002 Adler et al. ................. 435/7.1
2003/0040045 A1 * 2/2003 Zuker et al. ............... 435/69.1

* cited by examiner

*Primary Examiner*—Robert S. Landsman
(74) *Attorney, Agent, or Firm*—Hunton & Williams, LLP; Robin L. Teskin (57) ABSTRACT

The invention provides a series of chimeric $G_{\alpha15}$ protein variants that couple to certain GPCRs more efficiently than the native $G\alpha_{15}$ protein. These chimeric $G_{\alpha15}$ protein variants can be used to discover and analyze modulators of GPCRs (especially those that mediate taste perception).

6 Claims, 2 Drawing Sheets

METHODS OF CO-EXPRESSING UMAMI TASTE RECEPTORS AND CHIMERIC $G\alpha_{15}$ VARIANTS

CROSS-REFERENCE TO RELATED APPLICATIONS

This application claims priority to U.S. Provisional Application No. 60/339,472, filed Dec. 14, 2001, U.S. application Ser. No. 09/989,497, filed Nov. 21, 2001 now U.S. Pat. No. 7,041,457, which is a continuation-in-part of U.S. application Ser. No. 09/984,292, filed Oct. 29, 2001 now U.S. Pat. No. 6,818,747, which claims priority to U.S. Provisional Application No. 60/243,770, filed on Oct. 30, 2000, and all of these applications are incorporated herein by reference in their entirety.

FIELD OF INVENTION

This invention relates to Chimeric $G\alpha_{15}$ variants and their use in the discovery and analysis of modulators of G-protein coupled receptors. More specifically, the invention relates to chimeric $G\alpha_{15}$ variants wherein the C-terminal portion is that of another G protein and their use in GPCR based assays, especially chemosensory GPCRs, i.e. receptors that are involved in sensing of taste eliciting molecules, olfactants, and pheromones.

BACKGROUND OF INVENTION

G-protein-mediated signaling underlies the sensing of extracellular stimuli in all eukaryotic organisms. G proteins, which are heterotrimers of $G\alpha$, $G\beta$, and $G\gamma$ subunits, couple GPCRs to effector proteins such as phospholipase C and to intracellular second messengers such as $IP_3$. (Bourne, H. R., "How Receptors Talk to Trimeric G Proteins," Curr. Opin. Cell Biol., 9:134–142 (1997)). Activated GPCRs promote the displacement of bound GDP by GTP on the surface of the $G\alpha$ subunit and subsequent dissociation of the $G\alpha$ subunit from the $G\beta$ and $G\gamma$ subunits. Effector proteins are activated by binding to dissociated GTP-bound $G\alpha$ subunits and/or by binding to $G\beta$ and $G\gamma$ subunits.

Members of the $G_{\alpha q}$ class of G proteins couple GPCRs to phospholipase C, $IP_3$ synthesis, and calcium release from intracellular stores. The development of robust assays for calcium fluxes in living cells, such as those that make use of fluorescent calcium dyes or calcium-dependent reporter genes, has facilitated the functional characterization of many GPCRs that couple to members of this class of G proteins. Moreover, many GPCRs that do not normally couple to $G_{\alpha q}$-class G proteins can be linked to phospholipase C in two different ways: (1) using rodent $G_{\alpha 15}$ (or its human counterpart $G_{\alpha 16}$), a member of the $G_{\alpha q}$ class that couples to a large number of GPCRs in heterologous cells (Offermanns, S. and Simon, M. I., "G Alpha 15 and G alpha 16 Couple a Wide Variety of Receptors to Phospholipase C," J. Biol. Chem., 270:15175–15180 (1995)); (2) using hyperactive $G_{\alpha q}$ variants (See U.S. Ser. No. 09/984,292 filed Oct. 29, 2001, and U.S. Provisional 60/293,770 filed Oct. 30, 2000 by Yong Yao et al., both incorporated by reference in their entirety herein), or $G_{\alpha q}$ chimeras that incorporate C-terminal coupling determinants from members of other classes of G proteins (Conklin, B. R., Farfel, Z., Lustig, K. D., Julius, D. and Bourne, H. R., "Substitution of Three Amino Acids Switches Receptor Specificity of Gq Alpha to that of Gi Alpha," Nature, 363:274–276 (1993)). Recently, these two strategies have been combined to produce $G_{\alpha 16}$ chimeras that incorporate C-terminal coupling determinants from $G_{\alpha z}$, a member of the $G_{\alpha i}$ class of G proteins; such $G_{\alpha 16/z}$ chimeras have been shown to couple to several $G_{\alpha i}$-coupled receptors that do not couple to $G_{\alpha 16}$ (Mody, S. M., Ho, M. K., Joshi, S. A. and Wong, Y. H. "Incorporation of G Alpha(z)-Specific Sequence at the Carboxyl Terminus Increases the Promiscuity of G Alpha(16) Toward G(i)-Coupled Receptors," Mol. Pharmacol., 57:13–23 (2000)).

As described in the examples below, we have found, however, that the GPCRs that mediate sweet taste and umami taste (the savor of monosodium glutamate) in rats do not couple to $G_{\alpha 15}$, $G_{\alpha 16}$, or a $G_{\alpha 16/z}$ chimera. Consequently, we have generated a series of $G_{\alpha 15}$ chimeras in which the 5-residue C-terminal tail of $G_{\alpha 15}$ was replaced by the tails of all other G proteins, and have used these chimeras to develop assays for the rat sweet and umami taste receptors. This invention relates to these $G_{\alpha 15}$ chimeras and their use in functional assays for mammalian taste receptors and other GPCRs that do not couple efficiently to $G_{\alpha 15}$.

SUMMARY OF INVENTION

The present invention addresses the above described problems associated with the inability of native $G_{\alpha 15}$ to couple effectively with some GPCRs or GPCR combinations, especially some chemosensory GPCRs involved in taste or smell. Generally, the invention provides a $G\alpha_{15}$ protein variant that functionally couples to GPCRs not normally coupled by native $G\alpha_{15}$ and/or which couple with greater efficiency than native $G\alpha_{15}$ to a particular GPCR or GPCRs, e.g. sensory cell receptors such as taste GPCRs (TRs) and olfactory GPCRs (ORs). According to the invention, the functional coupling can be determined, for example, by measuring changes in intracellular IP3 or calcium. In a particular embodiment, the $G_{\alpha 15}$ protein variants can be expressed in mammalian cell lines or Xenopus oocytes, and then evaluated using calcium fluorescence imaging and electrophysiological recording.

The invention specifically provides chimeric variants of $G\alpha_{15}$ wherein one or more discrete portions of the native $G_{\alpha 15}$ protein are replaced with the corresponding portion of another G protein, and which optionally are further modified by one or more site specific mutations, which couple to one or more GPCRs not normally coupled by native $G\alpha_{15}$ and/or which exhibit increased coupling to at least one GPCR relative to the coupling of said at least one GPCR by native $G\alpha_{15}$, or which couple to a GPCR or GPCR combination not coupled by native $G_{\alpha 15}$.

In a more specific aspect, the invention provides chimeric variants of native $G\alpha_{15}$ wherein at least the last five carboxy-terminal amino acids are replaced by the corresponding at least five carboxy-terminal amino acids of another G protein, e.g. a G protein that normally couples the particular GPCR, e.g. a chemosensory GPCR such as a taste receptor, olfactory receptor or pheromone receptor.

In a still more specific aspect of the invention provided herein are chimeric $G\alpha_{15}$ variant proteins wherein the at least five carboxy-terminal amino acids of $G\alpha_{15}$ are replaced by the corresponding at least five carboxy-terminal amino acids of a G protein selected from the group consisting of $G\alpha_{i1}$, $G\alpha_q$, $G\alpha_s$, $G\alpha_{i3}$, $G\alpha_o$, $G\alpha_z$, $G\alpha_{12}$, $G\alpha_{13}$, and $G\alpha_{14}$, preferably $G\alpha_{i1}$. Optionally, these $G\alpha_{15}$ variants may be further modified by at least one substitution mutation which results in a chimeric $G\alpha_{15}$ variant protein that further enhances the ability of the resultant chimeric variant of $G\alpha_{15}$ protein to couple to a GPCR not normally coupled by nature Gα$_{15}$ and/or which couples with greater efficiency to a particular GPCR relative to native Gα$_{15}$.

Another aspect of the invention relates to nucleic acid sequences and expression vectors containing that encode a chimeric Gα$_{15}$ variant protein, wherein "chimeric" refers to the fact that one or more discrete portions of said Gα$_{15}$ protein are replaced by the corresponding portion or portions of another G protein, and which optionally may contain at least one substitution mutation, wherein the chimeric Gα15 variant protein encoded by said nucleic acid sequence couples to at least one GPCR not normally coupled by native Gα$_{15}$, and/or which couples more efficiently to at least one GPCR than native Gα$_{15}$ protein, e.g. a chemosensory GPCR such as a taste, olfactory or pheromone receptor.

In a more specific object of the invention, nucleic acid sequences are provided that encode chimeric Gα$_{15}$ variants wherein at least the 5 carboxy-terminal amino acids are replaced with that of another G protein, and which couple to a GPCR or GPCR combination, e.g. a chemosensory GPCR such as a taste receptor, olfactory receptor, or pheromone receptor not coupled by native Gα$_{15}$, or which couple more efficiently to a particular GPCR or GPCR combination, e.g. a chemosensory receptor such as a taste, olfactory or pheromone receptor more effectively than native Gα$_{15}$.

In a more preferred aspect of the invention, nucleic acid sequences and vectors are provided that encode a chimeric Gα$_{15}$ variant protein wherein at least the five carboxy-terminal amino acids are replaced by the corresponding carboxy-terminal amino acids of a G protein selected from the group consisting of Gα$_{i1}$, Gα$_{i3}$, Gα$_{q}$, Gα$_{s}$, Gα$_{i3}$, Gα$_{o}$, Gα$_{z}$, Gα$_{12}$, Gα$_{13}$, and Gα$_{14}$.

In another specific aspect of the invention, cells and cell lines are provided that express a chimeric variant Gα$_{15}$ protein wherein at least a portion, preferably at least the 5 carboxy-terminal amino acids are replaced by the corresponding portion of another G protein, e.g. Gα$_{i1}$, Gα$_{i3}$, Gα$_{q}$, Gα$_{s}$, Gα$_{i3}$, Gα$_{o}$, Gα$_{z}$, Gα$_{12}$, Gα$_{13}$, and Gα$_{14}$. Preferably, these cell lines will also express a particular GPCR or GPCR combination, i.e., a GPCR or GPCR combination that is coupled by said chimeric variant Gα$_{15}$ protein.

In a preferred aspect of the invention, the GPCR or GPCR combination coupled by the chimeric Gα$_{15}$ protein of the invention will be a chemosensory receptor, e.g. a taste receptor, olfactory receptor or pheromone receptor.

In another aspect of the invention, these Gα$_{15}$ chimeras can be expressed in mammalian cell lines and used for functional assays for GPCRs that involve, for example, measuring changes in intracellular IP$_3$ or calcium. In one embodiment, a Gα$_{15}$ chimera wherein the five-residue C-terminal tail has been replaced with that of another G protein, e.g. transducin or one of the G proteins previously identified can be co-expressed in a mammalian cell line with GPCRs that mediate sweet and umami taste, and the activity of these GPCRs can be measured using fluorescent calcium dyes to quantitate changes in intracellular calcium. In another aspect of the invention, these Gα$_{15}$ chimeras can be expressed in Xenopus oocytes and used for functional assays for GPCRs that involve, for example, measuring calcium-dependent ion channel activity e.g. functional assays using GPCRs that mediate sweet or umami taste or smell.

In yet another aspect of the invention, methods for the discovery and analysis of modulators (i.e., agonists, antagonists, and inverse agonists) of GPCRs using a Gα$_{15}$ chimera are provided. In one embodiment, modulators can be identified using a mammalian-cell-based assay that involves transiently transfected, or stably transfected, cDNAs or genes that encode Gα$_{15}$ chimeras. The GPCR modulators discovered using the disclosed assays are also encompassed.

BRIEF DESCRIPTION OF THE FIGURES

FIG. 1. Improved coupling of G$_{α15}$ chimeras to the rat T1R2/T1R3 sweet taste receptor. (Left panel) HEK-293 cells were transiently transfected with rat T1R2, T1R3, and each G$_{α15}$ chimera, and assayed for intracellular calcium increases in response to sucrose. The last five C-terminal residues of each G$_{α15}$ chimera are shown. (Right panel) HEK-293 cells were transiently transfected with rat T1R2, T1R3, and G$_{α15/i1}$, and assayed for increases in intracellular calcium in response to sweet taste stimuli. Activities in both panels represent the mean±s.e. number of responding cells for four imaged fields of approximately 1000 confluent cells. (Lowerpanel) Dose-response curves for HEK-293 cells transiently transfected with rat T1R2, T1R3, and G$_{α15/i1}$ to Acesulfame-K, sucralose, sucrose, and D-tryptophan are shown. Activities represent the mean±s.e. number of four determinations and are normalized to the maximal number of responding cells for each stimulus.

DETAILED DESCRIPTION OF THE INVENTION

As described above, the present inventors have discovered that chimeric Gα$_{15}$ variants can be constructed wherein at least a portion of said protein is replaced by the corresponding portion of another G protein, to produce a chimeric Gα$_{15}$ protein having altered binding properties, i.e. which couples better to a specific GPCR or GPCR combination than the wild-type Gα$_{15}$ protein, or which couples to a specific GPCR or GPCR combination which is not coupled by the wild-type Gα$_{15}$ protein.

The present inventors have discovered that chimeric Gα$_{15}$ protein, e.g. wherein the last five C-terminal residues are replaced with those of other G proteins exhibit altered coupling specificity and couple more efficiently to some GPCRs. In a preferred embodiment, Gα$_{15}$ chimeras are provided that comprise the carboxy 5 amino acids of Gα$_{i1}$.

The present invention also provides Gα$_{15}$ variants that exhibit at least 80% sequence identity to the polypeptide contained in SEQ ID NO: 2 discussed infra, which contain as the last 6 amino acids a polypeptide encoded by a sequence selected from SEQ ID NO:3, 4, 5, 6, 7, 8, 9, 10, 11 or 12 more preferably which exhibit at least 90% sequence identity, or even more preferably at least 95–99% sequence identity therewith.

The present invention also provides nucleic acid sequences that encode proteins exhibiting at least 80% sequence identity, more preferably at least 90% sequence identity, and still more preferably, at least 95–99% sequence identity to the nucleic acid sequence contained in SEQ ID NO:1 modified by the substitution of the last 6 codons with those contained in SEQ ID NO:3, 4, 5, 6, 7, 8, 9, 10, or 12.

Also included in the present invention are antibodies that selectively bind to the variant Gα$_{15}$ described herein, but not to the corresponding native Gα$_{15}$ protein. Such antibodies include whole, chimeric, humanized, tetramer, single chain, domain-deleted and other recombinant antibodies of any immunglobulin class, as well as antibody fragments, Fv, Fab', (Fab)'$_2$, etc. Preparation of such antibodies may be performed using any method known in the art (see, e.g., Kohler and Milstein, 1975, Nature 256: 495–97; Kozbar et al., 1983, Immunology Today 4: 72; Cole et al., pp. 77–96 in Monoclonal Antibodies and Cancer Therapy, 1985). Mice or other animals may be immunized with the G$\alpha_{15}$ protein variants of the invention in order to generate antibodies, which may be screened to identify those specific for the G$_q$ variants of the invention which also do not recognize the corresponding native G$_q$ protein.

The present invention also encompasses expression vectors including the nucleic acid sequences of the present invention operably linked to a promoter that functions in mammalian cells or Xenopus oocytes. A "promoter" is defined as an array of nucleic acid control sequences that direct transcription of a nucleic acid. A "promoter" includes all the necessary sequences near the start site of transcription, i.e., including a polymerase binding site. A promoter optionally includes distal enhancer or repressor elements which can be located as much as thousands base pairs away from the start site of transcription. Promoters may be either constitutive, i.e. active under most environmental and developmental conditions, or inducible, i.e., under specific environmental or developmental control. The term "operably linked" refers to a functional linkage between a nucleic acid expression control sequence (such as a promoter) and a second nucleic acid sequence, such as one encoding a variant G$_q$ protein as described in the present invention, wherein the expression control sequence directs transcription of the nucleic acid corresponding to the second sequence. An "expression vector" is a nucleic acid construct including a coding nucleic acid sequence according to the invention operably linked to a promoter, which allows for recombinant production of the variant G$_q$ proteins described herein. Expression vectors encompassed by the invention can be either incorporated into the genome of a host cell after transfection, or replicate extra-chromosomally. Expression vectors can be either plasmids, viruses or nucleic acid fragments. Alternatively, coding sequences can be incorporated into the genome behind a native promoter, thereby creating an operable expression linkage following transfection. Host cells transfected with the expression vectors of the invention are also encompassed.

The present invention also includes methods for identifying a compound that modulates GPCR signaling, e.g. sensory signaling in GPCR expressing cells, the method including the steps of: (1) contacting the compound with a cell expressing the G$\alpha_{15}$ variant protein according to the invention, preferably a chimeric G$\alpha_{15}$ protein described in the examples infra, and (2) determining the functional effect of said compound upon the G$\alpha_{15}$ protein variant. Typically, a cell expressing said G$\alpha_{15}$ variant protein is a transfected mammalian cell, e.g. a sensory cell, or other transfected cell suitable for making functional measurements of G protein activity, i.e., Xenopus oocyte. Functional effects of possible modulatory compounds may be determined by measuring changes in intracellular IP3 or Ca$^{2+}$. Functional effects may also be determined by measuring changes in the electrical activity of the cells expressing said G$_q$ variant protein or by observing modification of an intracellular effector enzyme. Possible modulatory compounds include agonists, antagonists, antibodies, small molecules and proteins.

Also included in the invention are methods for identifying a compound that interacts with the G$\alpha_{15}$ variant protein according to the invention, preferably a chimeric G$\alpha_{15}$ protein disclosed in the examples infra, including the steps of (1) contacting said G$_q$ variant protein with a test compound; and (2) detecting a binding interaction between said compound and said G$\alpha_{15}$ protein variant. Methods of detecting the binding of G$\alpha_{15}$ protein variants to compounds can be performed wherein said chimeric G$\alpha_{15}$ variant protein is linked to solid phase, either covalently or noncovalently.

The present invention also includes an artificial array of GPCRs functionally coupled to the G$\alpha_5$ variant according to the invention, preferably a chimeric G$\alpha_{15}$ variant disclosed in the examples, wherein said array is a model of a native arrangement of GPCRs. For instance, the native arrangement can be an arrangement of olfactory receptors (ORs) typically seen in a mammalian nose, or an arrangement of taste receptors typically seen on a mammalian tongue. However, other GPCRs are within the scope of the invention. Said taste receptors typically include at least one type of taste receptor selected from the group consisting of bitter, sweet, salty, umami and sour taste receptors, in light of the observations that such taste receptors are typically arranged in spatially organized manner. The artificial arrays of the present invention are useful for analyzing the response to different sensory compounds in relation to brain activity. Such arrays will be improved by the variant G$\alpha_{15}$ proteins of the present invention, which will simplify interpretation of results that might normally be complicated by the requirement for different G protein subunits for every GPCR in such an array.

It is also envisioned that the G$\alpha_{15}$ protein variants of the invention can be used in other types of functional assays such as biochemical binding assays, enzymatic assays, other cell-based assay, as well as with in vivo systems such as transgenic mice. Such assays are described in further detail below.

Thus, the invention substantially relates to the discovery that chimeric G$\alpha_{15}$ proteins can be produced having altered GPCR coupling properties, i.e. which couple to a specific GPCR or GPCR combination more efficiently than the native G$\alpha_{15}$ protein (having SEQ ID NO:2 set forth infra) or which couple to a specific GPCR or GPCR combination not coupled by the native G$\alpha_{15}$ protein having SEQ ID NO:2 infra.

In the context of the invention, "chimeric" refers to the fact that the variant G$\alpha_{15}$ protein comprises a portion, i.e. at least 5 amino acids at the carboxy terminal end that are identical to that of a G protein other than G$\alpha_{15}$.

The "other G protein" in the present invention encompasses G proteins of all G$\alpha$ subclasses, e.g. G$\alpha_{i1}$, G$\alpha_q$, G$\alpha_s$, G$\alpha_{i3}$, G$\alpha_z$, G$\alpha_o$, G$\alpha_{12}$, G$\alpha_{13}$, and G$\alpha_{14}$. The G protein may be of any species origin, but preferably will comprise a mammalian G protein, and most preferably will comprise a human, rat or mouse G protein different from G$\alpha_{15}$.

Additionally, the subject chimeric G$\alpha_{15}$ variants may comprise one or more substitution mutations, e.g. those that result in a variant having further enhanced GPCR coupling properties. For example, as disclosed in U.S. Ser. No. 09/984,292, filed Oct. 29, 2001 now U.S. Pat. No. 6,818,747, and 60/243,770, filed on Oct. 30, 2000, both incorporated by referenced in their entirety herein, it has been found that the mutation of mouse G$\alpha_q$ at position 66 (by replacing a Gly with an Asp) results in a G protein having enhanced promiscuity (couples better with specific GPCRs relative to wild-type G$\alpha_9$ protein. It is anticipated therefore that G$\alpha_{15}$ chimeric variants may be obtained that both comprise an altered carboxy-terminus (that of another G protein) and further comprise at least one substitution mutation, to produce a chimeric Gα$_{15}$ variant having further enhanced GPCR coupling activity vis-a-vis wild-type Gα$_{15}$ protein.

It has particularly been discovered that chimeric Gα$_{15}$ variants wherein the last 5 amino acids are replaced by the corresponding amino acid residues of another G protein can be produced that couple efficiently with chemosensory GPCRs, specifically, the taste receptors disclosed in Senomyx, U.S. Provisional Application No. 60/339,472, incorporated by reference in its entirely herein, that are not normally coupled by native Gα$_{15}$. For example, it has been found that chimeric Gα$_{15}$ variants according to the invention couple to T1R1 and T1R3 and give rise to a functional T1R1/T1R3 taste receptor (umami taste receptor).

Based thereon the invention is especially directed to the use of chimeric Gα$_{15}$ variants according to the invention in cell lines that express specific GPCRs or GPCR combinations, in order to produce cells that express a functional GPCR receptor or receptor complex, and to screen compound libraries for agonists or antagonists of specific GPCRs or GPCR combinations, e.g. chemosensory receptors such as taste, olfactory and pheromone receptors.

As noted, in a preferred embodiment, the inventive chimeric Gα$_{15}$ variants will be added or expressed in cells that express specific GPCRs, e.g. taste receptors such as T1R1, T1R2 and/or T1R3 or olfactory receptors.

Additional GPCRs can include those disclosed in U.S. patent application Ser. No. 09/510,332 filed Feb. 22, 2000 now abandoned; and U.S. Provisional Application Nos. 60/213,849 filed Jun. 23, 2000; 60/209,840 filed Jun. 6, 2000; 60/195,536 filed Apr. 7, 2000; 60/195,534 filed Apr. 7, 2000; 60/195,532 filed Apr. 7, 2000; which are herein incorporated by reference in their entirety.

Thus, the chimeric Gα$_{15}$ variants according to the invention can comprise amino acid substitutions at or near position 66, or at any other position that results in altered GPCR coupling actively by the variant Gα$_{15}$. Mutations can be identified and isolated using site directed or random mutagenesis according to techniques that are known in the art, including random saturation mutagenesis around the mutation sites described herein. The variants may comprise these one or more of these mutations alone or in combination with C-terminal substitutions. In another embodiment of the invention, Gα$_q$ and other G$_q$ subclass variants comprise C-terminal sequences derived from other G proteins.

For instance, it was disclosed in the Yao patent application incorporated by reference supra, that the Gly to Asp mutation at position 66 is synergistic with the replacement of the C-terminus of Gα$_q$ by that of transducin or Gα$_{olf}$. Gα$_q$ proteins containing C-terminal amino acids from transducin or Gα$_{olf}$ in combination with a Gly66 to Asp alteration show increased activity compared to individual chimeras alone.

Other mutations and substitutions are envisioned to be within the scope of the invention. For instance, it would be within the level of skill in the art to perform additional amino acid substitutions at other amino acid positions using known protocols of recombinant gene technology including PCR, gene cloning, site-directed mutagenesis of cDNA, transfection of host cells, and in-vitro transcription. The variants could then be screened for functional coupling to chemosensory receptors or other GPCRs as described herein. Further, additional C-terminal substitutions could be made from other G-protein molecules known in the art.

The present invention also provides Gα$_{15}$ variants that exhibit at least 80% sequence identity to the polypeptide encoded by SEQ ID NO: 1, which contain as the last 6 amino acids a polypeptide encoded by a sequence selected from SEQ ID NO:4, 5, 6, 7, 8, 9, 10, 11 or 12, more preferably which exhibit at least 90% sequence identity, or even more preferably at least 95–99% sequence identity therewith.

The present invention also provides nucleic acid sequences that encode proteins exhibiting at least 80% sequence identity, more preferably at least 90% sequence identity, and still more preferably, at least 95–99% sequence identity to the polypeptide encoded by SEQ ID NO:1 modified by the substitution of the last 6 codons with those contained in SEQ ID NO:4, 5, 6, 7, 8, 9, 10, 11 and 12.

The terms "identical" or "percent identity" in the context of two or more protein or nucleic acid sequences refers to sequences or subsequences that are the same or have a specified percentage of amino acid residues or nucleotides that are the same when compared and aligned for maximum correspondence over a comparison window or designated region, using either a sequence comparison algorithm that is known in the art or by manual inspection. Sequences with over 80% sequence identity are said to be "substantially identical." Optionally, the identity, exists over a region that is at least about 25–30 amino acids or nucleotides in length, or optionally over a region that is 75–100 amino acids or nucleotides in length.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. A "comparison window" as used herein includes reference to a segment of any one of the number of contiguous positions selected from the group consisting of from 25 to 500, usually about 50 to about 200, more usually about 100 to 150 in which a sequence may be compared to a reference sequence of the same number of contiguous positions after the two sequences are optimally aligned. Methods of alignment of sequences are well known in the art (see, e.g., Smith and Waterman, 1981, Adv. Appl. Math. 2: 482, Needleman and Wunsch, 1970, J. Mol. Biol. 48: 443, Pearson and Lipman, 1988, Proc. Natl. Acad. Sci. USA 85: 2444, and Current Protocols in Molecular Biology, Ausubel et al., 1995 Suppl.).

One example of a useful algorithm is PILEUP. PILEUP creates a multiple sequence alignment from a group of related sequences using progressive, pairwise alignments to show relationship and percent sequence identity, and can be obtained from the GCG sequence analysis software package, e.g., version 7.0 (Devereaux et al., 1984, Nuc. Acids Res. 12: 387–395). Another example of an algorithm that is suitable for determining percent sequence identity is the BLAST or BLAST 2.0 algorithm described in Altschul et al., 1977, Nuc. Acids Res. 25: 3389–3402 (1977) and Altschul et al., 1990, J. Mol. Biol. 215: 403–410, respectively. Software for performing BLAST analyses is publicly available through the National Center for Biotechnology Information website.

It is also envisioned that the Gα$_{15}$ protein variants of the invention could be used in other types of functional assays such as biochemical binding assays, enzymatic assays, other cell-based assay, as well as with in vivo systems such as transgenic mice. Such assays are described in further detail below.

In Vitro Binding Assays

GPCR transduction can be examined in vitro with soluble or solid state reactions, using the chimeric Gα$_{15}$ variant polypeptides of the invention. In a particular embodiment, GPCR ligand-binding domains can be used in vitro in soluble or solid state reactions to assay for ligand binding.

For instance, the N-terminal domain of a GPCR is predicted to be involved in ligand binding. For example, the T1Rs belong to a GPCR sub-family that is characterized by large, approximately 600 amino acid, extracellular N-terminal segments. These N-terminal segments are thought to form the ligand-binding domains, and are therefore useful in biochemical assays to identify GPCR agonists and antagonists. It is possible that the ligand-binding domain may be formed by additional portions of the extracellular domain, such as the extracellular loops of the transmembrane domain.

In vitro binding assays have been used with other GPCRs that are related to the T1Rs, such as the metabotropic glutamate receptors (see, e.g., Han and Hampson, *J. Biol. Chem.* 274:10008–10013 (1999)). These assays might involve displacing a radioactively or fluorescently labeled ligand, measuring changes in intrinsic fluorescence or changes in proteolytic susceptibility, etc.

Ligand binding to a hetero-multimeric complex of GPCR polypeptides can be tested in solution, in a bilayer membrane, optionally attached to a solid phase, in a lipid monolayer, or in vesicles. Binding of a modulator can be tested using, e.g., changes in spectroscopic characteristics (e.g., fluorescence, absorbence, refractive index) hydrodynamic (e.g., shape), chromatographic, or solubility properties.

In another embodiment of the invention, a GTP$\gamma^{35}$S assay may be used. As described above, upon activation of a GPCR, the G$\alpha$ subunit of the G protein complex is stimulated to exchange bound GDP for GTP. Ligand-mediated stimulation of G protein exchange activity can be measured in a biochemical assay measuring the binding of added radioactively labeled GTP$\gamma^{35}$S to the G protein in the presence of a putative ligand. Typically, membranes containing the chemosensory receptor of interest are mixed with a complex of G proteins. Potential inhibitors and/or activators and GTP$\gamma^{35}$S are added to the assay, and binding of GTP$\gamma^{35}$S to the G protein is measured. Binding can be measured by liquid scintillation counting or by any other means known in the art, including scintillation proximity assays (SPA). In other assays formats, fluorescently labeled GTP$\gamma$S can be utilized.

Fluorescence Polarization Assays

In another embodiment, Fluorescence Polarization ("FP") based assays may be used to detect and monitor ligand binding. Fluorescence polarization is a versatile laboratory technique for measuring equilibrium binding, nucleic acid hybridization, and enzymatic activity. Fluorescence polarization assays are homogeneous in that they do not require a separation step such as centrifugation, filtration, chromatography, precipitation, or electrophoresis. These assays are done in real time, directly in solution and do not require an immobilized phase. Polarization values can be measured repeatedly and after the addition of reagents since measuring the polarization is rapid and does not destroy the sample. Generally, this technique can be used to measure polarization values of fluorophores from low picomolar to micromolar levels. This section describes how fluorescence polarization can be used in a simple and quantitative way to measure the binding of ligands to the T1R polypeptides of the invention.

When a fluorescently labeled molecule is excited with plane polarized light, it emits light that has a degree of polarization that is inversely proportional to its molecular rotation. Large fluorescently labeled molecules remain relatively stationary during the excited state (4 nanoseconds in the case of fluorescein) and the polarization of the light remains relatively constant between excitation and emission. Small fluorescently labeled molecules rotate rapidly during the excited state and the polarization changes significantly between excitation and emission. Therefore, small molecules have low polarization values and large molecules have high polarization values. For example, a single-stranded fluorescein-labeled oligonucleotide has a relatively low polarization value but when it is hybridized to a complementary strand, it has a higher polarization value. When using FP to detect and monitor tastant-binding which may activate or inhibit the chemosensory receptors of the invention, fluorescence-labeled tastants or auto-fluorescent tastants may be used.

Fluorescence polarization (P) is defined as:

$$P = \frac{Int_\parallel - Int_\perp}{Int_\parallel + Int_\perp}$$

Where $\parallel$ is the intensity of the emission light parallel to the excitation light plane and Int $\perp$ is the intensity of the emission light perpendicular to the excitation light plane. P, being a ratio of light intensities, is a dimensionless number. For example, the Beacon® and Beacon 2000™ System may be used in connection with these assays. Such systems typically express polarization in millipolarization units (1 Polarization Unit=1000 mP Units).

The relationship between molecular rotation and size is described by the Perrin equation and the reader is referred to Jolley, M. E. (1991) in Journal of Analytical Toxicology, pp. 236–240, which gives a thorough explanation of this equation. Summarily, the Perrin equation states that polarization is directly proportional to the rotational relaxation time, the time that it takes a molecule to rotate through an angle of approximately 68.5° Rotational relaxation time is related to viscosity ($\eta$), absolute temperature (T), molecular volume (V), and the gas constant (R) by the following equation:

$$\text{Rotational Relaxation Time} = \frac{3\eta V}{RT}$$

The rotational relaxation time is small ($\approx$1 nanosecond) for small molecules (e.g. fluorescein) and large ($\approx$100 nanoseconds) for large molecules (e.g. immunoglobulins). If viscosity and temperature are held constant, rotational relaxation time, and therefore polarization, is directly related to the molecular volume. Changes in molecular volume may be due to interactions with other molecules, dissociation, polymerization, degradation, hybridization, or conformational changes of the fluorescently labeled molecule. For example, fluorescence polarization has been used to measure enzymatic cleavage of large fluorescein labeled polymers by proteases, DNases, and RNases. It also has been used to measure equilibrium binding for protein/protein interactions, antibody/antigen binding, and protein/DNA binding.

Solid State and Soluble High Throughput Assays

In yet another embodiment, the invention provides soluble assays using a GPCR/G$_q$ protein complex according to the invention; or a cell or tissue expressing said GPCR polypeptides and a G protein according to the invention. Preferably, the cell will comprise a cell line that stably expresses a functional GPCR, e.g. a taste receptor. In another embodiment, the invention provides solid phase based in vitro assays in a high throughput format, where the GPCR polypeptides, or cell or tissue expressing the GPCR polypeptide and a variant $G_q$ protein according to the invention is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 1000 to about 1500 different compounds. It is also possible to assay multiple compounds in each plate well. It is possible to assay several different plates per day; assay screens for up to about 6,000–20,000 different compounds is possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, The Adhesion Molecule Facts Book I (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.,* 85:2149–2154 (1963) (describing solid phase synthesis of, e.g., peptides); Geysen et al., *J. Immun. Meth.,* 102:259–274 (1987) (describing synthesis of solid phase components on pins); Frank & Doring, *Tetrahedron,* 44:60316040 (1988) (describing synthesis of various peptide sequences on cellulose disks); Fodor et al., *Science,* 251:767–777 (1991); Sheldon et al., *Clinical Chemistry,* 39(4):718–719 (1993); and Kozal et al., *Nature Medicine,* 2(7):753759 (1996) (all describing arrays of biopolymers fixed to solid substrates). Non-chemical approaches for fixing tag binders to substrates include other common methods, such as heat, cross-linking by UV radiation, and the like.

Cell-Based Assays

In one embodiment, a GPCR protein or polypeptide is transiently or stably expressed in a eukaryotic cell either in unmodified forms or as chimeric, variant or truncated receptors with or preferably without a heterologous, chaperone sequence that facilitates its maturation and targeting through the secretory pathway. Such GPCR polypeptides can be expressed in any eukaryotic cell, such as HEK-293 cells. The cells will further comprise a variant $G\alpha_{15}$ protein according to the invention, that is capable of coupling the chimeric receptor to an intracellular signaling pathway or to a signaling protein such as phospholipase C. In the case of taste receptors, preferably a cell will be produced that stably co-expresses a T1R1/T1R3 or T1R2/T1R3 as such cells have been found to exhibit enhanced responses to taste stimuli (relation to cells that transiently express the same T1R combination). Activation of T1R receptors in such cells can be detected using any standard method, such as by detecting changes in intracellular calcium by detecting FURA-2 dependent fluorescence in the cell. Such an assay is the basis of the experimental findings presented in this application.

Activated GPCR receptors often are substrates for kinases that phosphorylate the C-terminal tail of the receptor (and possibly other sites as well). Thus, activators will promote the transfer of $^{32}P$ from radiolabeled ATP to the receptor, which can be assayed with a scintillation counter. The phosphorylation of the C-terminal tail will promote the binding of arrestin-like proteins and will interfere with the binding of G proteins. For a general review of GPCR signal transduction and methods of assaying signal transduction, see, e.g., *Methods in Enzymology*, vols. 237 and 238 (1994) and volume 96 (1983); Bourne et al., *Nature,* 10:349:117–27 (1991); Bourne et al., *Nature,* 348:125–32 (1990); Pitcher et al., *Annu. Rev. Biochem.,* 67:653–92 (1998).

GPCR modulation may be assayed by comparing the response of GPCR polypeptides treated with a putative GPCR modulator to the response of an untreated control sample or a sample containing a known "positive" control. Such putative GPCR modulators can include molecules that either inhibit or activate GPCR polypeptide activity. In one embodiment, control samples (untreated with activators or inhibitors) are assigned a relative GPCR activity value of 100. Inhibition of a GPCR polypeptide is achieved when the GPCR activity value relative to the control is about 90%, optionally 50%, optionally 25–0%. Activation of a GPCR polypeptide is achieved when the GPCR activity value relative to the control is 110%, optionally 150%, 200–500%, or 1000–2000%.

Changes in ion flux may be assessed by determining changes in ionic polarization (i.e., electrical potential) of the cell or membrane expressing a GPCR polypeptide. One means to determine changes in cellular polarization is by measuring changes in current (thereby measuring changes in polarization) with voltage-clamp and patch-clamp techniques (see, e.g., the "cell-attached" mode, the "inside-out" mode, and the "whole cell" mode, e.g., Ackerman et al., *New Engl. J Med.,* 336:1575–1595 (1997)). Whole cell currents are conveniently determined using the standard. Other known assays include: radiolabeled ion flux assays and fluorescence assays using voltage-sensitive dyes (see, e.g., Vestergarrd-Bogind et al., *J. Membrane Biol.,* 88:67–75 (1988); Gonzales & Tsien, *Chem. Biol.,* 4:269277 (1997); Daniel et al., *J. Pharmacol. Meth.,* 25:185–193 (1991); Holevinsky et al., *J. Membrane Biology,* 137:59–70 (1994)).

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3, cGMP, or cAMP.

Preferred assays for GPCRs include cells that are loaded with ion or voltage sensitive dyes to report receptor activity. Assays for determining activity of such receptors can also use known agonists and antagonists for other G protein-coupled receptors as controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog.

Receptor activation initiates subsequent intracellular events, e.g., increases in second messengers. Activation of some G protein-coupled receptors stimulates the formation of inositol triphosphate (IP3) through phospholipase C-mediated hydrolysis of phosphatidylinositol (Berridge & Irvine, *Nature,* 312:315–21 (1984)). IP3 in turn stimulates the release of intracellular calcium ion stores. Thus, a change in cytoplasmic calcium ion levels, or a change in second messenger levels such as IP3 can be used to assess G protein-coupled receptor function. Cells expressing such G protein-coupled receptors may exhibit increased cytoplasmic calcium levels as a result of contribution from both calcium release from intracellular stores and extracellular calcium entry via plasma membrane ion channels.

In a preferred embodiment, GPCR polypeptide activity, e.g. T1R or OR receptor activity, is measured by stably or transiently co-expressing one or more GPCR genes, preferably stably, in a heterologous cell with a chimeric $G\alpha_{15}$ protein according to the invention that links the receptor to a phospholipase C signal transduction pathway (see Offermanns & Simon, *J. Biol. Chem.,* 270:15175–15180 (1995)). In a preferred embodiment, the cell line is HEK-293 and the G protein is a variant $G\alpha_{15}$ disclosed in the examples infra. Modulation of transduction is assayed by measuring changes in intracellular $Ca^{2+}$ levels, which change in response to modulation of the GPCR signal transduction pathway via administration of a molecule that associates with GPCR polypeptides. Changes in $Ca^{2+}$ levels are optionally measured using fluorescent $Ca^{2+}$ indicator dyes and fluorometric imaging.

In another embodiment, phosphatidyl inositol (PI) hydrolysis can be analyzed according to U.S. Pat. No. 5,436,128, herein incorporated by reference. Briefly, the assay involves labeling of cells with 3H-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist, to cpm in the presence of buffer control. Likewise, fold inhibition is determined by calculating the ratio of cpm in the presence of antagonist, to cpm in the presence of buffer control (which may or may not contain an agonist).

Other receptor assays can involve determining the level of intracellular cyclic nucleotides, e.g., cAMP or cGMP. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. In one embodiment, the changes in intracellular cAMP or cGMP can be measured using immunoassays. The method described in Offermanns & Simon, *J. Bio. Chem.,* 270:15175–15180 (1995), may be used to determine the level of cAMP. Also, the method described in Felley-Bosco et al., *Am. J. Resp. Cell and Mol. Biol.,* 11:159–164 (1994), may be used to determine the level of cGMP. Further, an assay kit for measuring cAMP and/or cGMP is described in U.S. Pat. No. 4,115,538, herein incorporated by reference.

In another embodiment, transcription levels can be measured to assess the effects of a test compound on signal transduction. A host cell containing GPCR polypeptides of interest and a variant $G_q$ protein according to the invention is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, luciferase, beta-galactosidase beta-lactamase and alkaline phosphatase. Furthermore, the protein of interest can be used as an indirect reporter via attachment to a second reporter such as green fluorescent protein (see, e.g., Mistili & Spector, *Nature Biotechnology*, 15:961–964 (1997)).

The amount of transcription is then compared to the amount of transcription in either the same cell in the absence of the test compound, or it may be compared with the amount of transcription in a substantially identical cell that lacks the $G_q$ variant polypeptide(s) of interest. A substantially identical cell may be derived from the same cells from which the recombinant cell was prepared but which had not been modified by introduction of heterologous DNA. Any difference in the amount of transcription indicates that the test compound has in some manner altered the activity of the GPCR polypeptides of interest.

Transgenic Non-Human Animals Expressing $G\alpha_{15}$ Proteins

Non-human animals expressing one or more variant G protein sequences of the invention can also be used for receptor assays. Such expression can be used to determine whether a test compound specifically binds to a mammalian taste GPCR receptor complex in vivo by contacting a non-human animal stably or transiently transfected with nucleic acids encoding GPCR receptors or ligand-binding regions thereof and a variant $G_q$ protein according to the invention with a test compound and determining whether the animal reacts to the test compound by specifically binding to the receptor polypeptide complex.

Animals transfected or infected with the vectors of the invention are particularly useful for assays to identify and characterize GPCRs that can bind thereto or to a specific or sets of receptors. Such vector-infected animals expressing human taste receptor sequences can be used for in vivo screening of taste stimuli and their effect on, e.g., cell physiology (e.g., on taste neurons), on the CNS, or behavior. Alternatively, stable cell lines that express a $G_q$ protein or combination thereof, can be used as nucleic transfer donors to produce cloned transgenic animals that stably express a particular variant $G_q$ protein or combination. Methods of using nucleic transfer to produce cloned animals that express a desired heterologous DNA are the subject of several issued U.S. patents granted to the University of Massachusetts (licensed to Advanced Cell Technology, Inc.) and Roslin Institute (licensed to Geron Corp.).

Means to infect/express the nucleic acids and vectors, either individually or as libraries, are well known in the art. A variety of individual cell, organ, or whole animal parameters can be measured by a variety of means. The $G\alpha_{15}$ nucleic acid sequences of the invention can be for example expressed in animal tissues by delivery with an infecting agent, e.g., adenovirus expression vector.

The endogenous $G\alpha_{15}$ protein genes can remain functional and wild-type (native) activity can still be present. Methods for the construction of non-human transgenic animals, particularly transgenic mice, and the selection and preparation of recombinant constructs for generating transformed cells are well known in the art.

Construction of a "knockout" cell and animal is based on the premise that the level of expression of a particular gene in a mammalian cell can be decreased or completely abrogated by introducing into the genome a new DNA sequence that serves to interrupt some portion of the DNA sequence of the gene to be suppressed. Also, "gene trap insertion" can be used to disrupt a host gene, and mouse embryonic stem (ES) cells can be used to produce knockout transgenic animals (see, e.g., Holzschu, *Transgenic Res* 6:97–106 (1997)). The insertion of the exogenous is typically by homologous recombination between complementary nucleic acid sequences. The exogenous sequence is some portion of the target gene to be modified, such as exonic, intronic or transcriptional regulatory sequences, or any genomic sequence which is able to affect the level of the target gene's expression; or a combination thereof. Gene targeting via homologous recombination in pluripotential embryonic stem cells allows one to modify precisely the genomic sequence of interest. Any technique can be used to create, screen for, propagate, a knockout animal, e.g., see Bijvoet, *Hum. Mol. Genet.* 7:53–62 (1998); Moreadith, *J. Mol. Med.* 75:208–216 (1997); Tojo, *Cytotechnology* 19:161–165 (1995); Mudgeft, *Methods Mol. Biol.* 48:167–184. (1995); Longo, *Transgenic Res.* 6:321–328 (1997); U.S. Pat. Nos. 5,616,491; 5,464,764; 5,631,153; 5,487,992; 5,627,059; 5,272,071; WO 91/09955; WO 93/09222; WO 96/29411; WO 95/31560; WO 91/12650.

The nucleic acids of the invention can also be used as reagents to produce "knockout" human cells and their progeny. Likewise, the nucleic acids of the invention can also be used as reagents to produce "knock-ins" in mice. The variant $G_q$ gene sequences can replace the orthologous $G_q$ sequence in the mouse genome. In this way, a mouse expressing a variant $G_q$ protein is produced. This mouse can then be used to analyze the function of the variant $G_q$ protein and to identify GPCRs that couple therewith.

Modulators

The compounds tested as modulators of a GPCR family member can be any small chemical compound, or a biological entity, such as a protein, nucleic acid or lipid. Essentially any chemical compound can be used as a potential modulator or ligand in the assays of the invention, although most often compounds that are soluble in aqueous solutions are tested. Assays can be designed to screen large chemical libraries by automating the assay steps and providing compounds from any convenient source; these assays are typically run in parallel (e.g., in microtiter formats on microtiter plates in robotic assays). It will be appreciated that chemical libraries can be synthesized by one of many chemical reactions (e.g. Senomyx proprietary chemistries). Additionally, there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one preferred embodiment, high throughput screening methods involve providing a combinatorial chemical or peptide library containing a large number of potential GPCR affecting compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual taste modulators.

Preferably, such libraries will be screened against cells or cell lines that stably express one or non particular GPCR and a variant $G\alpha_{15}$ protein according to the invention.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Thousands to millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.*, 37:487–493 (1991) and Houghton et al., *Nature*, 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci.*, 90:6909–6913 (1993)), vinylogous polypeptides (Hagihara et al., *J. Amer. Chem. Soc.*, 114:6568 (1992)), nonpeptidal peptidomimetics with glucose scaffolding (Hirschmann et al., J. Amer. Chem. Soc., 114:9217–9218 (1992)), analogous organic syntheses of small compound libraries (Chen et al., *J. Amer. Chem. Soc.,* 116:2661 (1994)), oligocarbamates (Cho et al., *Science,* 261:1303 (1993)), peptidyl phosphonates (Campbell et al., *J. Org. Chem.,* 59:658 (1994)), nucleic acid libraries (Ausubel, Berger and Sambrook, all supra), peptide nucleic acid libraries (U.S. Pat. No. 5,539,083), antibody libraries (Vaughn et al., *Nature Biotechnology,* 14(3):309–314 (1996) and PCT/US96/10287), carbohydrate libraries (Liang et al., *Science,* 274:1520–1522 (1996) and U.S. Pat. No. 5,593,853), small organic molecule libraries (benzodiazepines, Baum, *C&EN,* Jan 18, page 33 (1993); thiazolidinones and metathiazanones, U.S. Pat. No. 5,549,974; pyrrolidines, U.S. Pat. No. 5,525,735 and 5,519,134; morpholino compounds, U.S. Pat. No. 5,506,337; benzodiazepines, 5,288,514, and the like).

Devices for the preparation of combinatorial libraries are commercially available (see, e.g., 357 MPS, 390 MPS (Advanced Chem Tech, Louisville Ky.), Symphony (Rainin, Woburn, Mass.), 433A (Applied Biosystems, Foster City, Calif.), 9050 Plus (Millipore, Bedford, Mass.)). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences; Columbia, Md.; etc.).

The present invention also provides for kits for screening for modulators of specific GPCRs. Such kits can be prepared from readily available materials and reagents. For example, such kits can comprise any one or more of the following materials: a variant G protein according to he invention or a nucleic acid sequence encoding GPCR nucleic acids or proteins, reaction tubes, and instructions for testing the particular GPCR activity. Optionally, the kit contains a biologically active GPCR receptor or cell line that stably or transiently expresses a biologically active GPCR receptor, e.g. a T1R receptor. A wide variety of kits and components can be prepared according to the present invention, depending upon the intended user of the kit and the particular needs of the user.

The following examples serve merely to illustrate the invention, and should not be construed as limiting the scope of the invention in any way.

EXAMPLES

Example 1

Construction of $G\alpha_{15}$ Chimeras

In this example, the details of how the $G\alpha_{15}$ chimeras were made are presented. $G\alpha_{15}$ chimeras were generated by PCR with mutagenic 3' primers. The sequence of the parental $G\alpha_{15}$ clone (SEQ ID NO:1; amino acid sequence is SEQ ID NO:2) corresponds to databank sequences (e.g., accession BC005439) except for a silent single nucleotide polymorphism. The last six codons of $G\alpha_{15}$ and the sequences they were replaced with are shown below (SEQ ID NOS: 3–12). The $G\alpha_{15}$ chimeras were generated with 5' AscI sites (GGCGCGCCGCC joined to the start ATG) and 3α NotI sites (GCGGCCGC joined to the stop TGA) and cloned as AscI-NotI fragments in the AscI-NotI polylinker sites of the pEAK10 expression vector (Edge Biosystems).

```
G_α15 nucleotide sequence
atggcccggtccctgacttggggctgctgtccctggtgcctgacagaggaggagaagactgccgccagaa  (SEQ ID NO:1)

tcgaccaggagatcaacaggattttgttggaacagaaaaaacaagagcgcgaggaattgaaactcctgct gttgggcctggtgagagcgggaagagtacgttcatcaagcagatgcgcatcattcacggtgtgggctac tcggaggaggaccgcagagccttccggctgctcatctaccagaacatcttcgtctccatgcaggccatga tagatgcgatggaccggctgcagatccccttcagcaggcctgacagcaagcagcacgccagcctagtgat gacccaggaccctataaagtgagcacattcgagaagccatatgcagtggccatgcagtacctgtggcgg gacgcgggcatccgtgcatgctacgagcgaaggcgtgaattccaccttctggactccgcggtgtattacc tgtcacacctggagcgcatatcagaggacagctacatcccactgcgcaagacgtgctgcgcagtcgcat gcccaccacaggcatcaatgagtactgcttctccgtgaagaaaaccaaactgcgcatcgtggatgttggt ggccagaggtcagagcgtaggaaatggattcactgttttgagaacgtgattgccctcatctacctggcct ccctgagcgagtatgaccagtgcctagaggagaacgatcaggagaaccgcatggaggagagtctcgctct gttcagcacgatcctagagctgccctggttcaagagcacctcggtcatcctcttcctcaacaagacggac
```

-continued
```
atcctggaagataagattcacacctcccacctggccacatacttccccagcttccagggaccccggcgag acgcagaggccgccaagagcttcatcttggacatgtatgcgcgcgtgtacgcgagctgcgcagagcccca ggacggtggcaggaaaggctcccgcgcgcgccgcttcttcgcacacttcacctgtgccacggacacgcaa agcgtccgcagcgtgttcaaggacgtgcgggactcggtgctggcccggtacctggacgagatcaacctgc tgtga
```

G<sub>α15</sub> amino acid sequence
MARSLTWGCCPWCLTEEEKTAARIDQEINRILLEQKKQEREELKLLLLGPGESGKSTFIKQMRI (SEQ ID NO:2)

IHGVGYSEEDRRAFRLLIYQNIFVSMQAMIDAMDRLQIPFSRPDSKQHASLVMTQDPYKVSTFE

KPYAVAMQYLWRDAGIRACYERRREFHLLDSAVYYLSHLERISEDSYIPTAQDVLRSRMPTTGI

NEYCFSVKKTKLRIVDVGGQRSERRKWIHCFENVIALIYLASLSEYDQCLEENDQENRMEESLA

LFSTILELPWFKSTSVILFLNKTDILEDKIHTSHLATYFPSFQGPRRDAEAAKSFILDMYARVY

ASCAEPQDGGRKGSRARRFFAHFTCATDTQSVRSVFKDVRDSVLARYLDEINLL

G<sub>α</sub> tails (SEQ IDS NOS: 3-12)

| | |
|---|---|
| GAGATCAACCTGCTGTGA G<sub>α15</sub> | (SEQ ID NO: 3) |
| GACTGTGGCCTCTTCTGA G<sub>αi1</sub> | (SEQ ID NO: 4) |
| GAGTACAATCTGGTCTGA G<sub>αq</sub> | (SEQ ID NO: 5) |
| CAGTATGAGCTCTTGTGA G<sub>αs</sub> | (SEQ ID NO: 6) |
| GAGTGCGGCCTCTACTGA G<sub>α13</sub> | (SEQ ID NO: 7) |
| GGATGCGGACTCTACTGA G<sub>αo</sub> | (SEQ ID NO: 8) |
| TACATCGGCCTCTGCTGA G<sub>αz</sub> | (SEQ ID NO: 9) |
| GACATCATGCTCCAATGA G<sub>α12</sub> | (SEQ ID NO: 10) |
| CAACTAATGCTCCAATGA G<sub>α13</sub> | (SEQ ID NO: 11) |
| CACCAGGTTGAACTCTGA G<sub>α14</sub> | (SEQ ID NO: 12) |

Example 2

Characterization of Gα<sub>5</sub> Chimeras with Rat T1R2/T1R3

Figure 1:
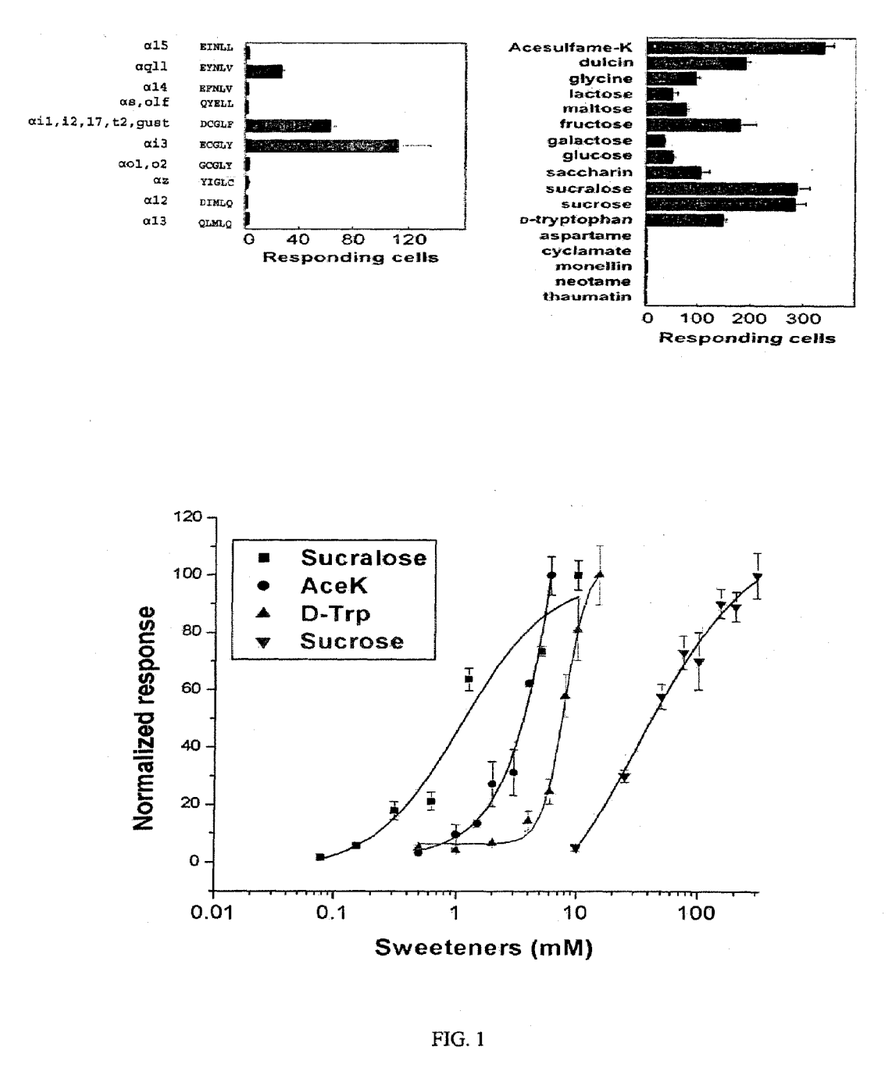

In this example, the use of a Gα<sub>15</sub> chimera to develop an improved assay for the rat T1R2/T1R3 sweet taste receptor is described. HEK-293 cells were transiently transfected with rat T1R2, T1R3, and each Gα<sub>15</sub> chimera, and assayed for intracellular calcium increases in response to 75 mM sucrose. Gα<sub>15</sub> chimeras with G<sub>αi</sub>-related or G<sub>αq</sub>-related tails coupled more efficiently to rat T1R2/T1R3 than Gα<sub>15</sub> (see FIG. 1, left panel). One of these Gα<sub>15</sub> chimeras, G<sub>α15/i1</sub> (which contains the C-terminal tail of transducin), was further characterized and used to demonstrate the rat T1R2/T1R3 recognizes all sweet taste stimuli tested (see FIG. 1, right panel). Moreover, rat T1R2/T1R3 dose responses to several sweet taste stimuli were determined using G<sub>α15/i1</sub> and found to correspond to rodent taste detection thresholds [Nelson et al., Cell 106:381–90 (2001); (Bachamanov et al., Chem. Senses 26:905–13 (2001)] (see FIG. 1, lower panel).

Rat T1R2 and T1R3 expression constructs were generated using the pEAK10 expression vector (Edge Biosystems). (Rat T1R1, T1R2, and T1R3 nucleic acid sequences are described in U.S. Provisional Application No. 60/339,472, incorporated by reference in its entirety herein). HEK-293 cells were grown and maintained at 37° C. in Dulbecco's Modified Eagle Medium (DMEM) supplemented with 10% FBS and MEM non-essential amino acids (Gibco BRL). For calcium-imaging experiments, cells were first seeded onto 24-well tissue-culture plates (approximately 100,000 cells per well), and transfected using Mirus Translt-293 (PanVera). Transfection efficiencies, which were estimated by cotransfection with an RFP expression vector, were typically approximately 70%. To minimize glutamate-induced and glucose-induced desensitization, supplemented DMEM was replaced with low-glucose DMEM supplemented with GlutaMAX and 10% dialyzed FBS (Gibco BRL) approximately 24 hours after transfection. 24 hours later, cells were loaded with the calcium dye fluo-4-AM (Molecular Probes), 3 μM in Dulbecco's PBS buffer (DPBS, GibcoBRL), for 1.5 hours at room temperature. After replacement with 250 μl DPBS, stimulation was performed at room temperature by addition of 200 μl DPBS supplemented with taste stimuli. Calcium mobilization was monitored on an Axiovert S100 microscope equipped with an inverted 10×/0.5 LWD piano fluor objective (Zeiss) and a cooled CCD camera (Princeton Instruments). Fluorescence images were acquired at 480 nm excitation and 535 nm emission, and analyzed with Imaging Workbench 4.0 software (Axon Instruments). T1R receptor activity was quantitated by counting the number of responding cells 30 seconds after stimulus addition. Stimuli used (and typical concentrations) were: Acesulfame-K (2.5 mM), aspartame (2.5 mM), cyclamate (5 mM), dulcin (0.1 mM), fructose (300 mM), galactose (300 mM), glucose (300 mM), lactose (250 mM), maltose (300 mM), monellin (0.01%), neotame (0.1 mM), perillartine (15 μM), saccharin (1 mM), sucralose (1 mM), sucrose (300 mM), thaumatin (0.01%), and D-tryptophan (10 mM).

Example 3

Characterization of $G\alpha_{15}$ Chimeras with Rat T1R1/T1R3

Figure 2:
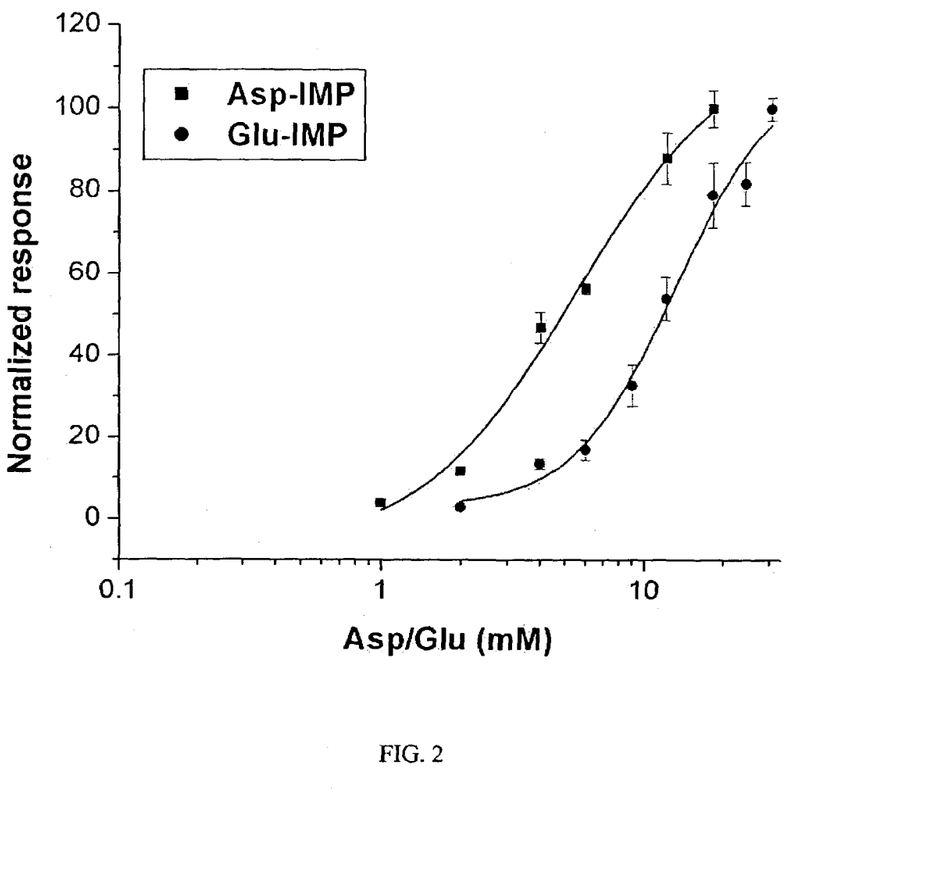
FIG. 2. Improved coupling of G$_{α15/i1}$ to the rat T1R1/T1R3 umami taste receptor. Dose-response curves for HEK-293 cells transiently transfected with rat T1R1, T1R3, and G$_{α15/i1}$, to L-aspartate and L-glutamate in the presence of 2.5 mM IMP. Activities represent the mean±s.e. number of four determinations and are normalized to the maximal number of responding cells for each stimulus.

In this example, the use of a $G\alpha_{15}$ chimera to develop an improved assay for the rat T1R1/T1R3 umami taste receptor is described. HEK-293 cells transiently cotransfected with rat T1R, T1R3, and $G_{\alpha 15}$ did not respond to any stimuli tested. In contrast, cells transiently transfected with rat T1R1, T1R3, and $G_{\alpha 15/i1}$ responded to the umami taste stimuli L-aspartate and L-glutamate in the presence of 2.5 mM IMP. The similar dose responses for rat T1R1/T1R3 (see FIG. 2) reflects their similar potency as taste stimuli in rodents. Transfection and assay conditions were as described in Example 2.

---

What is claimed:

1. A method for expressing a functional umami taste receptor comprising co-expressing (i) full-length unmodified rat, murine, rodent, human T1R1 and T1R3 taste receptor sequence in a cell which further expresses (ii) a chimeric G protein which is identical to the amino acid sequence recited in SEQ ID NO: 2 except for the substitution of an aspartic amino acid residue for the glycine residue at position 66, and the substitution of the last 6 amino acids of SEQ ID NO: 2 with the hexapeptide sequence encoded by the nucleic acid sequence contained in SEQ ID NO: 4.

2. The method of claim 1 wherein the cell is a mammalian cell, or an oocyte.

3. The method of claim 1 wherein the cell is a human cell.

4. The method of claim 1 wherein the cell is a HEK-293 cell.

5. The method of claim 1 wherein said full-length unmodified T1R1 and T1R3 sequences are human.

6. The method of claim 1 wherein said full-length unmodified T1R1 and T1R3 sequences are rat, or murine T1R1 and T1R3 sequences.

* * * * *

SEQUENCE LISTING

<160> NUMBER OF SEQ ID NOS: 13

<210> SEQ ID NO 1
<211> LENGTH: 1125
<212> TYPE: DNA
<213> ORGANISM: Mus musculus

<400> SEQUENCE: 1

```
atggcccggt ccctgacttg gggctgctgt ccctggtgcc tgacagagga ggagaagact      60
gccgccagaa tcgaccagga gatcaacagg attttgttgg aacagaaaaa acaagagcgc     120
gaggaattga aactcctgct gttggggcct ggtgagagcg ggaagagtac gttcatcaag     180
cagatgcgca tcattcacgg tgtgggctac tcggaggagg accgcagagc cttccggctg     240
ctcatctacc agaacatctt cgtctccatg caggccatga tagatgcgat ggaccggctg     300
cagatcccct tcagcaggcc tgacagcaag cagcacgcca gctagtgat gacccaggac      360 ccctataaag tgagcacatt cgagaagcca tatgcagtgg ccatgcagta cctgtggcgg     420
gacgcgggca tccgtgcatg ctacgagcga aggcgtgaat tccaccttct ggactccgcg     480
gtgtattacc tgtcacacct ggagcgcata tcagaggaca gctacatccc cactgcgcaa     540
gacgtgctgc gcagtcgcat gcccaccaca ggcatcaatg agtactgctt ctccgtgaag     600
aaaaccaaac tgcgcatcgt ggatgttggt ggccagaggt cagagcgtag gaaatggatt     660
cactgttttg agaacgtgat tgccctcatc tacctggcct ccctgagcga gtatgaccag     720
tgcctagagg agaacgatca ggagaaccgc atggaggaga gtctcgctct gttcagcacg     780
atcctagagc tgccctggtt caagagcacc tcggtcatcc tcttcctcaa caagacggac     840
atcctggaag ataagattca cacctcccac ctggccacat acttccccag cttccaggga     900
ccccggcgag acgcagaggc cgccaagagc ttcatcttgg acatgtatgc gcgcgtgtac     960
gcgagctgcg cagagcccca ggacggtggc aggaaaggct cccgcgcgcg ccgcttcttc    1020
gcacacttca cctgtgccac ggacacgcaa agcgtccgca gcgtgttcaa ggacgtgcgg    1080
gactcggtgc tggcccggta cctggacgag atcaacctgc tgtga                    1125
```

<210> SEQ ID NO 2
<211> LENGTH: 374
<212> TYPE: PRT
<213> ORGANISM: Mus musculus

<400> SEQUENCE: 2

```
Met Ala Arg Ser Leu Thr Trp Gly Cys Cys Pro Trp Cys Leu Thr Glu
  1               5                  10                  15

Glu Glu Lys Thr Ala Ala Arg Ile Asp Gln Glu Ile Asn Arg Ile Leu
             20                  25                  30

Leu Glu Gln Lys Lys Gln Glu Arg Glu Glu Leu Lys Leu Leu Leu Leu
         35                  40                  45
```

Gly Pro Gly Glu Ser Gly Lys Ser Thr Phe Ile Lys Gln Met Arg Ile
            50                  55                  60

Ile His Gly Val Gly Tyr Ser Glu Glu Asp Arg Arg Ala Phe Arg Leu
 65                  70                  75                  80

Leu Ile Tyr Gln Asn Ile Phe Val Ser Met Gln Ala Met Ile Asp Ala
                     85                  90                  95

Met Asp Arg Leu Gln Ile Pro Phe Ser Arg Pro Asp Ser Lys Gln His
                100                 105                 110

Ala Ser Leu Val Met Thr Gln Asp Pro Tyr Lys Val Ser Thr Phe Glu
            115                 120                 125

Lys Pro Tyr Ala Val Ala Met Gln Tyr Leu Trp Arg Asp Ala Gly Ile
            130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Ser Glu Asp Ser Tyr Ile
                165                 170                 175

Pro Thr Ala Gln Asp Val Leu Arg Ser Arg Met Pro Thr Thr Gly Ile
                180                 185                 190

Asn Glu Tyr Cys Phe Ser Val Lys Lys Thr Lys Leu Arg Ile Val Asp
                195                 200                 205

Val Gly Gly Gln Arg Ser Glu Arg Arg Lys Trp Ile His Cys Phe Glu
            210                 215                 220

Asn Val Ile Ala Leu Ile Tyr Leu Ala Ser Leu Ser Glu Tyr Asp Gln
225                 230                 235                 240

Cys Leu Glu Glu Asn Asp Gln Glu Asn Arg Met Glu Glu Ser Leu Ala
                245                 250                 255

Leu Phe Ser Thr Ile Leu Glu Leu Pro Trp Phe Lys Ser Thr Ser Val
                260                 265                 270

Ile Leu Phe Leu Asn Lys Thr Asp Ile Leu Glu Asp Lys Ile His Thr
                275                 280                 285

Ser His Leu Ala Thr Tyr Phe Pro Ser Phe Gln Gly Pro Arg Arg Asp
        290                 295                 300

Ala Glu Ala Ala Lys Ser Phe Ile Leu Asp Met Tyr Ala Arg Val Tyr
305                 310                 315                 320

Ala Ser Cys Ala Glu Pro Gln Asp Gly Gly Arg Lys Gly Ser Arg Ala
                325                 330                 335

Arg Arg Phe Phe Ala His Phe Thr Cys Ala Thr Asp Thr Gln Ser Val
                340                 345                 350

Arg Ser Val Phe Lys Asp Val Arg Asp Ser Val Leu Ala Arg Tyr Leu
            355                 360                 365

Asp Glu Ile Asn Leu Leu
        370

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      Ga15 tail nucleotide sequence

<400> SEQUENCE: 3
gagatcaacc tgctgtga                                                  18

<210> SEQ ID NO 4

```
<211> LENGTH: 18
<212> TYPE: DNA
<213> ORGANISM: Artificial Sequence
<220> FEATURE:
<223> OTHER INFORMATION: Description of Artificial Sequence: Synthetic
      Gai1 tail nucleotide sequence

<400> SEQUENCE: 4
gactgtggcc tcttctga                                                   18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      Gaq tail nucleotide sequence

<400> SEQUENCE: 5
gagtacaatc tggtctga                                                   18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      Gas tail nucleotide sequence

<400> SEQUENCE: 6
cagtatgagc tcttgtga                                                   18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      Gai3 tail nucleotide sequence

<400> SEQUENCE: 7
gagtgcggcc tctactga                                                   18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      Ga0 tail nucleotide sequence

<400> SEQUENCE: 8
ggatgcggac tctactga                                                   18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      Gaz tail nucleotide sequence

<400> SEQUENCE: 9
tacatcggcc tctgctga                                                   18

<210> SEQ ID NO 10
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      Ga12 tail nucleotide sequence

<400> SEQUENCE: 10
gacatcatgc tccaatga                                                     18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      Ga13 tail nucleotide sequence

<400> SEQUENCE: 11
caactaatgc tccaatga                                                     18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      Ga14 tail nucleotide sequence

<400> SEQUENCE: 12
caccaggttg aactctga                                                     18

<210> SEQ ID NO 13
<211> LENGTH: 11
<212> TYPE: DNA
<213> ORGANISM: Artificial Sequence
<220> FEATURE:
<223> OTHER INFORMATION: Description of Artificial Sequence:
      Illustrative AscI site oligonucleotide

<400> SEQUENCE: 13
ggcgcgccgc c                                                            11
```